United States Patent
Shah et al.

(10) Patent No.: US 7,094,256 B1
(45) Date of Patent: Aug. 22, 2006

(54) COATINGS FOR IMPLANTABLE MEDICAL DEVICE CONTAINING POLYCATIONIC PEPTIDES

(75) Inventors: Ashok A. Shah, San Jose, CA (US); Eugene T. Michal, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 350 days.

(21) Appl. No.: 10/320,899

(22) Filed: Dec. 16, 2002

(51) Int. Cl.
*A61F 2/06* (2006.01)

(52) U.S. Cl. .................... 623/1.46; 623/1.48; 623/1.49; 428/476.3; 428/476.6; 428/522; 427/2.24

(58) Field of Classification Search ................ 623/1.46, 623/1.48, 1.49; 428/523, 522, 476.3, 476.6; 427/2.24
See application file for complete search history.

(56) References Cited

U.S. PATENT DOCUMENTS

| | | | |
|---|---|---|---|
| 2,072,303 A | 3/1937 | Herrmann et al. | 128/335.5 |
| 2,386,454 A | 10/1945 | Frosch et al. | 260/78 |
| 3,773,737 A | 11/1973 | Goodman et al. | 260/78 |
| 3,835,175 A | 9/1974 | Carpino et al. | 260/463 |
| 3,849,514 A | 11/1974 | Gray, Jr. et al. | 260/857 |
| 4,226,243 A | 10/1980 | Shalaby et al. | 128/335.5 |
| 4,329,383 A | 5/1982 | Joh | 428/36 |
| 4,343,931 A | 8/1982 | Barrows | 528/291 |
| 4,529,792 A | 7/1985 | Barrows | 528/291 |
| 4,611,051 A | 9/1986 | Hayes et al. | 528/295.3 |

(Continued)

FOREIGN PATENT DOCUMENTS

| | | |
|---|---|---|
| DE | 42 24 401 | 1/1994 |
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 6656 023 | 8/1995 |
| EP | 0 677 332 A2 | 10/1995 |
| EP | 0 701 802 | 3/1996 |

(Continued)

OTHER PUBLICATIONS

U.S. Pat. Application No. 10/176,499, filed Jun. 21, 2002, Hossainy et al.

Anderson et al., *Close Relation of Endothelial Function in the Human Coronary and Peripheral Circulations*, JACC 26(5): 1235–1241 (1995).

Anderson et al., *Nitric–Oxide and Nitrovasodilators: Similarities, Differences and Potential Interactions*, JACC 24(2): 555–556 (1994).

Anonymous, Reducing the pH of a peptide oligomer to prepare for systemic delivery, Defensive Publication, Research Disclosure p. 905 (Aug. 2003).

Anonymous, *Cardiologists Draw —Up The Dream Stent*, Clinica 710: 15 (Jun. 17, 1996), http://www.dialogweb.com/cgi/document?reg=1061848202959, printed Aug. 25, 2003 (2 pages).

(Continued)

*Primary Examiner*—D. Lawrence Tarazano
(74) *Attorney, Agent, or Firm*—Squire, Sanders & Dempsey L.L.P.

(57) ABSTRACT

Coatings for implantable medical devices and methods for fabricating the same are disclosed. The coatings include carboxylated acrylates and polycationic peptides, for example R7.

22 Claims, 1 Drawing Sheet

U.S. PATENT DOCUMENTS

| | | | |
|---|---|---|---|
| 4,656,242 A | 4/1987 | Swan et al. | 528/295.3 |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,908,404 A * | 3/1990 | Benedict et al. | 525/54.11 |
| 4,917,309 A | 4/1990 | Zander et al. | 241/5 |
| 4,931,287 A | 6/1990 | Bae et al. | 424/484 |
| 4,941,870 A | 7/1990 | Okada et al. | 600/36 |
| 4,977,901 A | 12/1990 | Ofstead | 128/772 |
| 5,019,096 A | 5/1991 | Fox, Jr. et al. | 623/1 |
| 5,025,001 A | 6/1991 | Loscalzo et al. | 514/91 |
| 5,100,992 A | 3/1992 | Cohn et al. | 424/501 |
| 5,112,457 A | 5/1992 | Marchant | 204/165 |
| 5,129,980 A | 7/1992 | Sissons | 528/272 |
| 5,133,742 A | 7/1992 | Pinchuk | 623/1 |
| 5,147,981 A | 9/1992 | Buet et al. | 424/486 |
| 5,155,137 A | 10/1992 | Keefer et al. | 514/611 |
| 5,163,952 A | 11/1992 | Froix | 623/1 |
| 5,165,919 A | 11/1992 | Sasaki et al. | 424/488 |
| 5,187,183 A | 2/1993 | Loscalzo et al. | 514/400 |
| 5,202,129 A | 4/1993 | Samejima et al. | 424/489 |
| 5,258,020 A | 11/1993 | Froix | 623/1 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | 525/437 |
| 5,328,471 A | 7/1994 | Slepian | 604/101 |
| 5,330,768 A | 7/1994 | Park et al. | 424/501 |
| 5,356,890 A | 10/1994 | Loscalzo et al. | 514/210 |
| 5,366,997 A | 11/1994 | Keefer et al. | 614/611 |
| 5,380,299 A | 1/1995 | Fearnot et al. | 604/265 |
| 5,395,326 A | 3/1995 | Haber et al. | 427/2.24 |
| 5,405,919 A | 4/1995 | Keefer et al. | 525/377 |
| 5,424,077 A | 6/1995 | Lajoie | 424/641 |
| 5,428,070 A | 6/1995 | Cooke et al. | 514/557 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,482,720 A | 1/1996 | Murphy et al. | 424/489 |
| 5,485,496 A | 1/1996 | Lee et al. | 378/64 |
| 5,516,881 A | 5/1996 | Lee et al. | 528/320 |
| 5,536,723 A | 7/1996 | Loscalzo et al. | 514/247 |
| 5,543,099 A | 8/1996 | Zhang et al. | 264/115 |
| 5,569,463 A | 10/1996 | Helmus et al. | 424/426 |
| 5,578,073 A | 11/1996 | Haimovich et al. | 623/1 |
| 5,584,877 A | 12/1996 | Miyake et al. | 623/1 |
| 5,605,696 A | 2/1997 | Eury et al. | 424/423 |
| 5,607,467 A | 3/1997 | Froix | 623/1 |
| 5,609,629 A | 3/1997 | Fearnot et al. | 623/1 |
| 5,610,241 A | 3/1997 | Lee et al. | 525/411 |
| 5,616,338 A | 4/1997 | Fox, Jr. et al. | 424/423 |
| 5,624,411 A | 4/1997 | Tuch | 604/265 |
| 5,628,730 A | 5/1997 | Shapland et al. | 604/21 |
| 5,639,441 A | 6/1997 | Sievers et al. | 424/9.3 |
| 5,644,020 A | 7/1997 | Timmermann et al. | 528/288 |
| 5,649,977 A | 7/1997 | Campbell | 623/1 |
| 5,650,442 A | 7/1997 | Mitchell et al. | 514/611 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,735,897 A | 4/1998 | Buirge | 623/12 |
| 5,746,998 A | 5/1998 | Torchilin et al. | 424/9.4 |
| 5,759,205 A | 6/1998 | Valentini | 623/16 |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,804,318 A * | 9/1998 | Pinchuk et al. | 428/421 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,852,058 A | 12/1998 | Cooke et al. | 514/564 |
| 5,854,376 A | 12/1998 | Higashi | 528/288 |
| 5,858,746 A | 1/1999 | Hubbell et al. | 435/177 |
| 5,861,168 A | 1/1999 | Cooke et al. | 424/424 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,874,165 A * | 2/1999 | Drumheller | 428/308.4 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | 424/489 |
| 5,891,459 A | 4/1999 | Cooke et al. | 424/439 |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,945,452 A | 8/1999 | Cooke et al. | 514/564 |
| 5,955,508 A | 9/1999 | Lorens et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,060,534 A * | 5/2000 | Ronan et al. | 523/113 |
| 6,063,432 A | 5/2000 | Maxwell et al. | 426/656 |
| 6,077,543 A | 6/2000 | Gordon et al. | 424/489 |
| 6,080,488 A | 6/2000 | Hostettler et al. | 428/423.3 |
| 6,095,134 A | 8/2000 | Sievers et al. | 128/200.14 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,117,872 A | 9/2000 | Maxwell et al. | 514/249 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |

| | | | | | |
|---|---|---|---|---|---|
| 6,120,904 A | 9/2000 | Hostettler et al. ........ 428/423.3 | 6,625,486 B1 | 9/2003 | Lundkvist et al. ............ 604/21 |
| 6,121,027 A | 9/2000 | Clapper et al. ............. 435/180 | 6,645,135 B1 | 11/2003 | Bhat ............................. 600/3 |
| 6,129,761 A | 10/2000 | Hubbell ........................ 623/11 | 6,645,195 B1 | 11/2003 | Bhat et al. .................. 604/528 |
| 6,136,333 A | 10/2000 | Cohn et al. ................. 424/423 | 6,656,216 B1 | 12/2003 | Hossainy et al. .......... 623/1.13 |
| 6,143,354 A | 11/2000 | Koulik et al. .............. 427/2.24 | 6,656,506 B1 | 12/2003 | Wu et al. .................... 424/489 |
| 6,153,252 A | 11/2000 | Hossainy et al. ............. 427/2.3 | 6,660,034 B1 | 12/2003 | Mandrusov et al. ........ 623/1.42 |
| 6,159,978 A | 12/2000 | Myers et al. ............. 514/252.1 | 6,663,662 B1 | 12/2003 | Pacetti et al. .............. 623/1.13 |
| 6,165,212 A | 12/2000 | Dereume et al. .......... 623/1.13 | 6,663,880 B1 | 12/2003 | Roorda et al. .............. 424/423 |
| 6,172,167 B1 | 1/2001 | Stapert et al. .............. 525/420 | 6,666,880 B1 | 12/2003 | Chiu et al. ................. 623/1.11 |
| 6,177,523 B1 | 1/2001 | Reich et al. ................ 525/459 | 6,673,154 B1 | 1/2004 | Pacetti et al. ............... 118/500 |
| 6,180,632 B1 | 1/2001 | Myers et al. ............. 514/252.1 | 6,673,385 B1 | 1/2004 | Ding et al. ................ 427/2.28 |
| 6,183,783 B1 | 2/2001 | Benoit et al. ............... 424/497 | 6,689,099 B1 | 2/2004 | Mirzaee ..................... 604/107 |
| 6,203,551 B1 | 3/2001 | Wu .............................. 606/108 | 6,695,920 B1 | 2/2004 | Pacetti et al. ............... 118/500 |
| 6,211,249 B1 | 4/2001 | Cohn et al. .............. 514/772.1 | 6,706,013 B1 | 3/2004 | Bhat et al. ................ 604/96.01 |
| 6,214,901 B1 | 4/2001 | Chudzik et al. ............ 523/113 | 6,709,514 B1 | 3/2004 | Hossainy ..................... 118/52 |
| 6,228,346 B1 | 5/2001 | Zhang et al. ................. 424/45 | 6,712,845 B1 | 3/2004 | Hossainy ................... 623/1.42 |
| 6,231,600 B1 | 5/2001 | Zhong ........................ 623/1.42 | 6,713,119 B1 | 3/2004 | Hossainy et al. .......... 427/2.25 |
| 6,240,616 B1 | 6/2001 | Yan ............................ 29/527.2 | 6,716,444 B1 | 4/2004 | Castro et al. ............... 424/422 |
| 6,245,753 B1 | 6/2001 | Byun et al. ................... 514/58 | 6,723,120 B1 | 4/2004 | Yan ............................ 623/1.15 |
| 6,245,760 B1 | 6/2001 | He et al. ................... 514/234.8 | 6,733,768 B1 | 5/2004 | Hossainy et al. ........... 424/426 |
| 6,248,129 B1 | 6/2001 | Froix ......................... 623/1.42 | 6,740,040 B1 | 5/2004 | Mandrusov et al. ........ 600/439 |
| 6,251,136 B1 | 6/2001 | Guruwaiya et al. ........ 623/1.46 | 6,743,462 B1 | 6/2004 | Pacetti ....................... 427/2.24 |
| 6,254,632 B1 | 7/2001 | Wu et al. ................... 623/1.15 | 6,749,626 B1 | 6/2004 | Bhat et al. .................. 523/1.1 |
| 6,258,121 B1 | 7/2001 | Yang et al. ................. 623/1.46 | 6,753,071 B1 | 6/2004 | Pacetti ....................... 428/212 |
| 6,258,371 B1 | 7/2001 | Koulik et al. ............... 424/422 | 6,758,859 B1 | 7/2004 | Dang et al. ................. 623/1.15 |
| 6,262,034 B1 | 7/2001 | Mathiowitz et al. .......... 514/44 | 6,759,054 B1 | 7/2004 | Chen et al. ................. 424/423 |
| 6,270,788 B1 | 8/2001 | Koulik et al. ............... 424/423 | 6,764,505 B1 | 7/2004 | Hossainy et al. .......... 623/1.15 |
| 6,277,449 B1 | 8/2001 | Kolluri et al. ............... 427/289 | 2001/0007083 A1 | 7/2001 | Roorda ...................... 623/1.15 |
| 6,283,947 B1 | 9/2001 | Mirzaee ..................... 604/264 | 2001/0014717 A1 | 8/2001 | Hossainy et al. ............. 525/60 |
| 6,283,949 B1 | 9/2001 | Roorda ................... 604/288.02 | 2001/0018469 A1 | 8/2001 | Chen et al. ................. 523/121 |
| 6,284,305 B1 | 9/2001 | Ding et al. ................ 427/2.28 | 2001/0020011 A1 | 9/2001 | Mathiowitz et al. .......... 514/44 |
| 6,287,628 B1 | 9/2001 | Hossainy et al. ............. 427/2.3 | 2001/0029351 A1 | 10/2001 | Falotico et al. ......... 604/103.02 |
| 6,299,604 B1 | 10/2001 | Ragheb et al. .............. 604/265 | 2001/0037145 A1 | 11/2001 | Guruwaiya et al. ........ 623/1.15 |
| 6,306,166 B1 | 10/2001 | Barry et al. ................ 623/1.46 | 2001/0051608 A1 | 12/2001 | Mathiowitz et al. .......... 514/44 |
| 6,306,176 B1 | 10/2001 | Whitbourne ............. 623/23.59 | 2002/0005206 A1 | 1/2002 | Falotico et al. ............. 128/898 |
| 6,306,993 B1 | 10/2001 | Rothbard et al. ........... 526/304 | 2002/0007213 A1 | 1/2002 | Falotico et al. ............. 623/1.21 |
| 6,331,313 B1 | 12/2001 | Wong et al. ................ 424/427 | 2002/0007214 A1 | 1/2002 | Falotico ..................... 623/1.21 |
| 6,335,029 B1 | 1/2002 | Kamath et al. ............. 424/423 | 2002/0007215 A1 | 1/2002 | Falotico et al. ............. 623/1.21 |
| 6,344,035 B1 | 2/2002 | Chudzik et al. ............ 604/265 | 2002/0009604 A1 | 1/2002 | Zamora et al. ............. 428/450 |
| 6,346,110 B1 | 2/2002 | Wu .............................. 606/108 | 2002/0016625 A1 | 2/2002 | Falotico et al. ............. 623/1.13 |
| 6,358,556 B1 | 3/2002 | Ding et al. ................ 427/2.24 | 2002/0032414 A1 | 3/2002 | Ragheb et al. .............. 604/265 |
| 6,379,381 B1 | 4/2002 | Hossainy et al. .......... 623/1.42 | 2002/0032434 A1 | 3/2002 | Chudzik et al. .......... 304/890.1 |
| 6,387,379 B1 | 5/2002 | Goldberg et al. ........... 424/400 | 2002/0051730 A1 | 5/2002 | Bodnar et al. ................ 422/33 |
| 6,419,692 B1 | 7/2002 | Yang et al. ................. 623/1.15 | 2002/0071822 A1 | 6/2002 | Uhrich .................... 424/78.37 |
| 6,451,373 B1 | 9/2002 | Hossainy et al. .......... 427/2.25 | 2002/0077693 A1 | 6/2002 | Barclay t al. .............. 623/1.13 |
| 6,482,834 B1 | 11/2002 | Spada et al. ................ 514/311 | 2002/0082679 A1 | 6/2002 | Sirhan et al. ............... 623/1.15 |
| 6,494,862 B1 | 12/2002 | Ray et al. ................. 604/96.01 | 2002/0087123 A1 | 7/2002 | Hossainy et al. ........... 604/198 |
| 6,503,538 B1 | 1/2003 | Chu et al. ................... 424/497 | 2002/0091433 A1 | 7/2002 | Ding et al. ................... 623/1.2 |
| 6,503,556 B1 | 1/2003 | Harish et al. .............. 427/2.24 | 2002/0094440 A1 | 7/2002 | Llanos et al. ............... 428/421 |
| 6,503,954 B1 | 1/2003 | Bhat et al. ................ 514/772.2 | 2002/0111590 A1 | 8/2002 | Davila et al. ............... 604/265 |
| 6,506,437 B1 | 1/2003 | Harish et al. .............. 427/2.25 | 2002/0120326 A1 | 8/2002 | Michal ...................... 623/1.15 |
| 6,524,347 B1 | 2/2003 | Myers et al. ............. 251/252.1 | 2002/0123801 A1 | 9/2002 | Pacetti et al. ............... 623/1.46 |
| 6,527,801 B1 | 3/2003 | Dutta ......................... 623/1.46 | 2002/0142039 A1 | 10/2002 | Claude ....................... 424/486 |
| 6,527,863 B1 | 3/2003 | Pacetti et al. ............... 118/500 | 2002/0155212 A1 | 10/2002 | Hossainy ................... 427/2.25 |
| 6,528,526 B1 | 3/2003 | Myers et al. ............... 214/311 | 2002/0165608 A1 | 11/2002 | Llanos et al. ............... 623/1.45 |
| 6,530,950 B1 | 3/2003 | Alvarado et al. .......... 623/1.13 | 2002/0176849 A1 | 11/2002 | Slepian ..................... 424/93.7 |
| 6,530,951 B1 | 3/2003 | Bates et al. ................. 623/1.45 | 2002/0183581 A1 | 12/2002 | Yoe et al. ...................... 600/3 |
| 6,540,776 B1 | 4/2003 | Sanders Millare et al. 623/1.15 | 2002/0188037 A1 | 12/2002 | Chudzik et al. ............ 523/112 |
| 6,544,223 B1 | 4/2003 | Kokish .................... 604/103.01 | 2002/0188277 A1 | 12/2002 | Roorda et al. .............. 604/523 |
| 6,544,543 B1 | 4/2003 | Mandrusov et al. ........ 424/422 | 2003/0004141 A1 | 1/2003 | Brown ........................ 514/152 |
| 6,544,582 B1 | 4/2003 | Yoe ............................ 427/2.24 | 2003/0028243 A1 | 2/2003 | Bates et al. ................. 623/1.15 |
| 6,555,157 B1 | 4/2003 | Hossainy ................... 427/2.24 | 2003/0028244 A1 | 2/2003 | Bates et al. ................. 623/1.15 |
| 6,558,733 B1 | 5/2003 | Hossainy et al. .......... 427/2.24 | 2003/0031780 A1 | 2/2003 | Chudzik et al. ............. 427/2.1 |
| 6,565,659 B1 | 5/2003 | Pacetti et al. ............... 118/500 | 2003/0032767 A1 | 2/2003 | Tada et al. ................. 528/310 |
| 6,572,644 B1 | 6/2003 | Moein ........................ 623/1.11 | 2003/0036794 A1 | 2/2003 | Ragheb et al. ............. 623/1.15 |
| 6,585,755 B1 | 7/2003 | Jackson et al. ............ 623/1.15 | 2003/0039689 A1 | 2/2003 | Chen et al. ................. 424/468 |
| 6,585,765 B1 | 7/2003 | Hossainy et al. .......... 623/1.45 | 2003/0040712 A1 | 2/2003 | Ray et al. .................... 604/173 |
| 6,585,926 B1 | 7/2003 | Mirzaee ..................... 264/400 | 2003/0040790 A1 | 2/2003 | Furst ......................... 623/1.11 |
| 6,605,154 B1 | 8/2003 | Villareal .................... 118/500 | 2003/0059520 A1 | 3/2003 | Chen et al. .................. 427/2.1 |
| 6,616,765 B1 | 9/2003 | Wu et al. ................... 623/1.45 | 2003/0060877 A1 | 3/2003 | Falotico et al. ............. 623/1.42 |
| 6,623,448 B1 | 9/2003 | Slater ....................... 604/95.01 | 2003/0065377 A1 | 4/2003 | Davila et al. ............... 623/1.13 |

| | | | |
|---|---|---|---|
| 2003/0072868 A1 | 4/2003 | Harish et al. ............... 427/2.24 |
| 2003/0073961 A1 | 4/2003 | Happ .......................... 604/274 |
| 2003/0083646 A1 | 5/2003 | Sirhan et al. ............. 604/891.1 |
| 2003/0083739 A1 | 5/2003 | Cafferata .................... 623/1.42 |
| 2003/0097088 A1 | 5/2003 | Pacetti ......................... 604/19 |
| 2003/0097173 A1 | 5/2003 | Dutta ......................... 623/1.38 |
| 2003/0099712 A1 | 5/2003 | Jayaraman ................... 424/486 |
| 2003/0105518 A1 | 6/2003 | Dutta ......................... 623/1.38 |
| 2003/0113439 A1 | 6/2003 | Pacetti et al. ............... 427/2.24 |
| 2003/0150380 A1 | 8/2003 | Yoe ............................ 118/423 |
| 2003/0157241 A1 | 8/2003 | Hossainy et al. ........... 427/2.24 |
| 2003/0158517 A1 | 8/2003 | Kokish ................. 604/103.01 |
| 2003/0190406 A1 | 10/2003 | Hossainy et al. .......... 427/2.25 |
| 2003/0207020 A1 | 11/2003 | Villareal .................... 427/2.24 |
| 2003/0211230 A1 | 11/2003 | Pacetti et al. ............... 427/2.24 |
| 2004/0018296 A1 | 1/2004 | Castro et al. ............... 427/2.25 |
| 2004/0029952 A1 | 2/2004 | Chen et al. .................. 514/449 |
| 2004/0047978 A1 | 3/2004 | Hossainy et al. ............ 427/2.1 |
| 2004/0047980 A1 | 3/2004 | Pacetti et al. ............... 427/2.25 |
| 2004/0052858 A1 | 3/2004 | Wu et al. ..................... 424/490 |
| 2004/0052859 A1 | 3/2004 | Wu et al. ..................... 424/490 |
| 2004/0054104 A1 | 3/2004 | Pacetti ........................ 526/242 |
| 2004/0060508 A1 | 4/2004 | Pacetti et al. ................ 118/264 |
| 2004/0062853 A1 | 4/2004 | Pacetti et al. ................ 427/2.1 |
| 2004/0063805 A1 | 4/2004 | Pacetti et al. ............... 523/113 |
| 2004/0071861 A1 | 4/2004 | Mandrusov et al. ........ 427/2.24 |
| 2004/0072922 A1 | 4/2004 | Hossainy et al. ........... 523/113 |
| 2004/0073298 A1 | 4/2004 | Hossainy ................... 623/1.46 |
| 2004/0086542 A1 | 5/2004 | Hossainy et al. ........... 424/423 |
| 2004/0086550 A1 | 5/2004 | Roorda et al. .............. 424/448 |
| 2004/0096504 A1 | 5/2004 | Michal ........................ 424/471 |
| 2004/0098117 A1 | 5/2004 | Hossainy et al. .......... 623/1.42 |

FOREIGN PATENT DOCUMENTS

| | | |
|---|---|---|
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1273 314 | 1/2003 |
| JP | 2001-190687 | 7/2001 |
| RU | 872531 | 10/1981 |
| RU | 876663 | 10/1981 |
| RU | 905228 | 2/1982 |
| RU | 790725 | 2/1983 |
| RU | 1016314 | 5/1983 |
| RU | 811750 | 9/1983 |
| RU | 1293518 | 2/1987 |
| WO | WO 91/12846 | 9/1991 |
| WO | WO 94/09760 | 5/1994 |
| WO | WO 94/28721 | 12/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/16983 | 5/1997 |
| WO | WO 97/45105 | 12/1997 |
| WO | WO 97/46590 | 12/1997 |
| WO | WO 98/06389 | 2/1998 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/49199 | 11/1998 |
| WO | WO 99/00070 | 1/1999 |
| WO | WO 99/01118 | 1/1999 |
| WO | WO 99/38546 | 8/1999 |
| WO | WO 99/59433 | 11/1999 |
| WO | WO 99/63981 | 12/1999 |
| WO | WO 99/66921 | 12/1999 |
| WO | WO 00/02599 | 1/2000 |
| WO | WO 00/12147 | 3/2000 |
| WO | WO 00/18446 | 4/2000 |
| WO | WO 00/46395 | 8/2000 |
| WO | WO 00/64506 | 11/2000 |
| WO | WO 00/74701 | 12/2000 |
| WO | WO 01/01890 | 1/2001 |
| WO | WO 01/08684 | 2/2001 |
| WO | WO 01/13957 | 3/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/62297 | 8/2001 |
| WO | WO 01/74414 | 10/2001 |
| WO | WO 02/03890 | 1/2002 |
| WO | WO 02/26162 | 4/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/039612 | 5/2003 |
| WO | WO 03/037223 | 8/2003 |
| WO | WO 03/080147 | 10/2003 |
| WO | WO 03/082368 | 10/2003 |
| WO | WO 04/000383 | 12/2003 |
| WO | WO 04/009145 | 1/2004 |

OTHER PUBLICATIONS

Anonymous, *Heparin–coated stents cut complications by 30*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Agent Delivery or Coated Stent*(Abstract 434009), Res. Disclos., pp. 974–975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al, *Preparation of cross–linked aliphatic polyester and application to thermo–responsive material*, Journal of Controlled Release 32:87–96 (1994).

Barath et al., *Low Dose of Antitumor Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25: 1259–1274 (Oct. 1991).

Bode–Boger et al., *Elevated L–Arginine/Dimethylarginine Ratio Contributes to Enhanced Systemic NO Production by Dietary L–Arginine in Hypercholesterolemic Rabbits*, Biochem. And Biophys. Res. Comm.219:598–603 (1996).

Bodmer et al., *Enhanced Recognition of a Modified Peptide Antigen by Cytotoxic T Cells Specific for Influenza Nucleoprotein*, Cell 52:253–258 (1988).

Boger et al, *An Endogenous Inhibitor of Nitric Oxide Synthase Regulates Endothelial Adhesiveness for Monocytes*, JACC 36(7):2287–2295 (2000).

Boger et al., *Asymmetric Dimethylarginine (ADMA):A Novel Risk Factor for Endothelial Dysfunction: Its Role in Hypercholestrolemia*, Clr. 98: 1842–1847 (1998).

Boger et al., *Asymmetric Dimethylarginine: A Novel Risk Factor for Endothelial Dysfunction*, Cir. 56(8):1–32 (1997).

Boger et al., *Restoring Vascular Nitric Oxide Formation by L–Arginine Improves the Symptoms of Intermittent Claudication in Patients With Peripheral Arterial Occlusive Disease*, J. Am. Coll. Cardiol. 32:1336–1344 (1998).

Boger et al., *The Endogenous NO Synthase Inhibitor Asymmetric Dimethyl–L–Arginine (ADMA) Regulates Endothelial NO Production and Adhesiveness for Monocytes*(Abstract J5), Nitric Oxide 2: 126 (1998).

Brochure, FreeZone CFC–Free Freeze Dry Systems, A Complete Guide to Laboratory Lyophilization Products, LABCONCO (2000).

Candipan et al., *Dietary L–Arginine Attenuates Macrophage Infiltration and Intimal Hyperplasia After Balloon Injury*-(Abstract 765–2), JACC 25:275A (1995).

Candipan et al., *Regression or Progression Dependency on Vacular Nitric Oxide*, Arterioscler. Thromb. Vasc. Biol. 16(1):44–*50 (1996).

Chan et al., *Asymmetric Dimethylarginine Increases Mononuclear Cell Adhesiveness in Hypercholestrolemic Humans*, Arterioscler. Thromb. Vasc. Biol. 20:1040–1046 (2002).

Chung et al., *Inner core design for drug delivery control of thermo–responsive polymeric micelles*, Journal of Controlled Release 65:93–103 (2000).

Cooke et al. *Arginine: A New Therapy for Atherosclerosis?* Cir. 95(2):311–312 (1997).

Cooke et al, *Cytoprotective Effects of Nitric Oxide*, Cir. 88(5)1:2451–2454 (1993).

Cooke et al., *Derangements of the Nitric Oxide Synthase Pathway, L–Arginine, and Cardiovascular Diseases*, Circ. 96(2):379–382 (1997).

Cooke et al., *Diffuse Coronary Artery Disease and Endothelial Dysfunction: From Follow Function*, ACC Curr. J. Rev. pp. 19–25 (Nov./Dec. 2000).

Cooke et al., *Regression and Progression: Dependency Upon NO (Abstract)*, J. Investi. Med. 43(2) Suppl. 2:211A (1995).

Cooke et al., *The Role of Endothelium–Derived Nitric Oxide in Atherosclerosis*, Adv. Vasc. Path. 1150:3–14 (1997).

Cooke, *Does ADMA Cause Endothelial Dysfunction?*, Arterioscler. Thromb. Vasc. Biol. 20:2032–2037 (2002).

Cooke, *Enhancement of Endogenous Vascular Nitric Oxide: A New Therapeutic Strategy for Restenosis*, (Abstract 301), Eur. J. Clin Investi. 28:A53 (1998).

Cooke, *Is Atherosclerosis an Arginine Deficiency Disease?*, J. Investi. Med. 46(8):2377–380 (1998).

Cooke, *Nutriceuticals for Cardiovascular Health*, Am. J. Cardio., 82(10A):43S–46S (1998).

Cooke, *Role of Nitric Oxide in Progression and Regression of Atheroslerosis*, West. J. Med. 164(5):419–424 (1996).

Cooke, *The 1998 Nobel Prize in Medicine: Clinical Implications for 1999 and Beyond*, Vasc. Med. 4:57–60 (1999).

Coooke, *The Endothelium: A New Target for Therapy*, Vasc. Med. 5:49–43 (2000).

Cooke, *The Pathophysiology Of Peripheral Arterial Disease: Rational Targets for Drug Intervention*, Vasc. Med. 2:227–230 (1997).

Creager et al., *L–Arginine Improvs Endothelium–Dependent Vasodilation in Hypercholesterolemic Humans*, J. Clin Investi. 90:1248–1253 (1992).

Dev et al., *Kinetics of Drug Delivery to the Arterial Wall Via Polyurethane–Coated Removable Nitinol Stent: Comparative Study of Two Drugs*, Catheterization and Cardiovascular Diagnosis 34:272–278 (1995).

Dichek et al., *Seeding of Intravascular Stents with Genetically Engineered Endothelial Cells*, Circ. 80(5): 1347–1353 (Nov. 1989).

Drexler et al., *Effect of L–Arginine on Coronary Endothelial Function in Cardiac Transplant Recipients: Relation to Vessel Wall Morphology*, Circ. 89(4): 1615–1623 (1994).

Drexler et al, *Endothelial Dysfuntion in the Coronary Circulation After Cardiac Transplantation: Effect of L–Arginine*(Abstract 1356), Circ. 86(4): Supp: 1418 (1992).

Dulak et al., *Nitric Oxide Induces the Synthesis of Vascular Endothelial Growth Factor by Rat Vascular Smooth Muscle Cells*, Arterioscler. Thromb. Vasc. Biol. 20:659–666 (2002).

Eigler et al., *Local Arterial Wall Drug Delivery from a Polymer Coated Removable Metallic Stent: Kinetics, Distribution, and Bioactivity of Forskolin*, JACC 4A(701–1), Abstract (Feb. 1994).

Gaiser et al., *Lethal Short–Limbed Dwarfism in Transgenic Mice with an Arginine to Cysteine Substitution in Alpha–I (II) Procollagen*(Abstract 3369), Mol. Biol. Cell 7:579A (1996).

Ganz et al., *Coronary Vasospasm in Human —The Role of Atheroslerosis and of Impaired Endothelial Vasodilator Function*, Basic Res. Cardiol. 86(Suppl 2):215–222 (1991).

Gregory et al., *Enhanced Nitric Oxide Production Induced by the Administration of L–Arginine Doe Not Inhibit Arterial Neointimal Formation After Overwhelming Alloimmune Injury*, J. Heart Lung Transplant. 15(1)Part 1:58–66 (1996).

Gregory et al., *Nitric Oxide Induced by the Administrator of L–Arginine Does Not Inhibit Arterial Neointimal Formation Following Alloimmune Injury*(Abstract 41), J. Heart Lung Transplant 14 (1)Part 2:S45 (1995).

Heescheri et al., *Hypercholesteolemia Impairs Angiogenic Response to Hind Limb Ischemia*: Role of ADMA (Abstract 2490), Circ. Ii–473 (1999).

Helmus, *Overview of Biomedical Materials*, MRS Bulletin, pp. 33–38 (Sep. 1991).

Herdeg et al., *Antiproliferative Stent Coatings: Taxol and Related Compounds*, Semin. Intervent. Cardiol. 3:197–199 (1998).

Ho et al., *Dietary L–Arginine Reverses the Inhibitory Effect of Asymmetri Dimethylarginine on Angiogenesis in Hypercholesterolemia*(Abstract 407–2), JACC 33: 1A (1999).

*http://physiololgy.cup.cam.ac.uk/Proceedings/Abstracts/523P/Birmingham/Files/S32.html*, Musialek et al., *The Nitric Oxide Donor Sodium Nitroprusside Increases Heart Rate In The Absence Of Changes in Arterial Blood Pressure When Applied Topically To The Sino–Atrial Node In The Anaesthetized Pig*, J. Physiol. (2000), printed Jun. 12, 2001.

* cited by examiner

COATINGS FOR IMPLANTABLE MEDICAL DEVICE CONTAINING POLYCATIONIC PEPTIDES

BACKGROUND OF THE INVENTION

1. Field of the Invention

This invention is directed to coatings for implantable medical devices, for example stents, containing polycationic peptides such as polymers and/or oligomers of L-arginine.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are: capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to, Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Local administration of therapeutic agents via stents has shown some favorable results in reducing restenosis. However, development of restenosis remains a persistent problem which has not been significantly alleviated by therapeutic substances which are currently used in the market. Accordingly, there is a great need for better and more effective therapeutic compositions and methods of administering the compositions for the effective treatment of restenosis.

SUMMARY

A method for fabricating a coating for an implantable medical device is provided. The method comprises depositing a layer including a polycationic peptide on the device, and depositing a layer including a carboxylated acrylic polymer over the layer including the polycationic peptide.

Examples of a suitable polycationic peptide include poly(L-arginine), poly(D-arginine), poly(D,L-arginine), poly(L-lysine), poly(D-lysine), poly(δ-guanidino-α-aminobutyric acid), and a racemic mixture of poly(L-arginine) and poly(D-arginine). An example of a suitable carboxylated acrylic polymer includes a carboxylated acrylic polymer having a formula wherein each X, X', and X" is independently, a hydrogen atom or an alkyl group; Q is an alkoxy group or 2-amino-2-methyl propane sulfonyl group; Q' is an unsubstituted or substituted phenyl group or a carboxy group; each R and R' is, independently a $C_1$ to $C_{12}$ straight chained or branched aliphatic radical; and x, y, and z are integers, where y ≠0.

A coating for an implantable medical device is provided. The coating comprises a region including a carboxylated acrylic polymer disposed over a region including a polycationic peptide.

DETAILED DESCRIPTION

Figure 1:
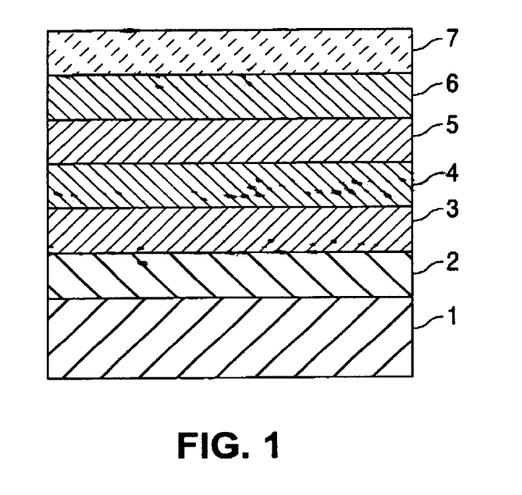
FIG. 1 shows schematically a cross-section of a stent coating according to an embodiment of the present invention.

According to embodiments of the present invention, a coating for an implantable medical device, such as a stent, can be a sandwiched multi-layer structure. The sandwich structure of the coating according to one embodiment of the present invention is illustrated by FIG. 1. To fabricate the stent coating, the following procedure can be utilized. As a first step, stent 1 is rinsed in i-propyl alcohol, sonicated, and treated by argon plasma using techniques known to those having ordinary skill in the art. As a second step, a primer layer 2 can be optionally formed on the stent surface. To form the primer layer, a polymer can be dissolved in a solvent, or a mixture of solvents, and the resulting polymer solution can be applied on the stent surface, for example, by spraying or immersing the stent in the polymer solution.

Next, a first drug layer 3 can be applied on the stent. To make the drug layer, the drug can be dissolved in a suitable solvent to form a solution. Examples of solvents that can be used to dissolve the drug include water, N,N-dimethylacetamide (DMAC), dimethylsulfoxide (DMSO), methanol and mixtures thereof. Optionally, the drug can be blended with a polymer such as poly(ethylene-co-vinyl alcohol) or poly(ethylene glycol), followed by dissolving the drug-polymer blend in a suitable solvent such as DMAC.

The solution containing the drug can be applied on the stent surface or on the primer layer 2, for example, by spraying or immersing the stent in the solution.

As a next step, a first intermediate polymer layer 4 can be formed over the first drug layer 3. To form the first intermediate polymer layer 4, a polymer can be dissolved in a solvent, or a mixture of solvents, and the resulting polymer solution can be applied on the first drug layer 3, for example, by spraying or immersing the stent in the polymer solution.

Steps of forming the drug layer and the intermediate polymer layer can be repeated in an alternating order until a desired amount of the drug is incorporated in the stent coating. For example, a second drug layer 5 can be formed over the first intermediate polymer layer 4, followed by a second intermediate polymer layer 6 and so forth. Typically, in a coating applied on a 13 mm TETRA® stent (available from Guidant Corporation), each drug layer can contain between about 25 and 50 micrograms (μg) of the drug, and each intermediate polymer layer can contain between about 30 and 60 μg of the polymer.

Finally, a topcoat layer 7 can be optionally formed as the outermost layer of the stent coating. To form the topcoat layer 7, a polymer can be dissolved in a solvent, or a mixture of solvents, and the resulting polymer solution can be applied, for example, by spraying or immersing the stent in the polymer solution.

One example of a drug or therapeutic substance that can be used is a polycationic peptide or a mixture of several polycationic peptides. Representative examples of suitable polycationic peptides include poly(L-arginine), poly(D-arginine), poly(D,L-arginine), poly(L-lysine), poly(D-lysine), poly(δ-guanidino-α-aminobutyric acid), racemic mixtures of poly(L-arginine) and poly(D-arginine), chitosan, and mixtures thereof.

L-arginine, also known as R, Arg, or 2-amino-5-guanidinovaleric acid, is an amino acid having a formula Polymers and/or oligomers of L-, D-, and D, L-arginine that can be used are referred to as "PArg" and comprise a plurality of repeating monomeric amino acid units connected with peptide bonds, each unit including a 1-guanidinopropyl radical having the structure —CH$_2$—CH$_2$—CH$_2$—NH—C(NH$_2$)=NH. Consequently, PArg has a general formula (I)

where "p" is an integer that can be within a range of 5 and 1,000, e.g., between 6 and 20. For example, a heptamer (R7) (p=7), or a nonamer (R9) (p=9), can be used.

The terms "polymers and/or oligomers of D-, L-, and/or D, L-arginine," "poly(L-arginine)," "poly(D-arginine)," "poly(D,L-arginine)," and "PArg" used in the present application are intended to include L-, D-, and/or D,L-arginine in both its polymeric and oligomeric form.

Poly(ethylene-co-vinyl alcohol) (EVAL) is one example of a polymer that can be used for fabricating the optional primer layer and the optional topcoat layer 7. EVAL has the general formula —[CH$_2$—CH$_2$]$_m$—[CH$_2$—CH(OH)]$_n$— and is a product of hydrolysis of ethylene-vinyl acetate copolymers. EVAL may also include a terpolymer having up to about 5 molar % of units derived from styrene, propylene and other suitable unsaturated monomers. A brand of copolymer of ethylene and vinyl alcohol distributed commercially under the trade name EVAL by EVAL Company of America (EVALCA) of Houston, Tex. can be used.

Representative examples of other polymers suitable for fabricating the optional primer layer and the optional topcoat layer include polyacrylates (such as poly(methyl methacrylate), poly(ethyl methacrylate), poly(butyl methacrylate), poly(ethyl methacrylate-co-butyl methacrylate), poly(2-hydroxyethyl methacrylate), poly (methyl methacrylate-co-2-hydroxyethyl methacrylate) and poly(butyl methacrylate-co-2-hydroxyethyl methacrylate)), poly(hydroxyvalerate), poly(L-lactic acid), polycaprolactone, poly(lactide-co-glycolide), poly (hydroxybutyrate), poly(glycerol-sebacate), poly (hydroxybutyrate-co-valerate), polydioxanone, polyorthoester, polyanhydride, poly(glycolic acid), poly(D, L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose and fluorinated polymers and/or copolymers, for example, poly(vinylidene fluoride) (PVDF) and poly(vinylidene fluoride-co-hexafluoro propene) (PVDF-HFP), and blends of polyacrylates and fluorinated polymers and/or copolymers.

To make intermediate polymer layers, carboxylated acrylic polymers or blends thereof can be used. Examples of suitable carboxylated acrylic polymers include polymers with a general formula (II)

wherein:
  each X, X', and X" is independently a hydrogen atom (acrylates) or an alkyl group such as a methyl group CH$_3$ (methacrylates);
  Q is an alkoxy group —OR or a 2-amino-2-methyl propane sulfonyl group —NH—C(CH$^3$)$_2$—CH$_2$—SO$_3$;
  Q' is an unsubstituted or substituted phenyl group or a carboxy group —COOR';
  each R and R' is independently a C$_1$ to C$_{12}$ straight chained or branched aliphatic radical; and
  x, y, and z are integers, where y≠0.

The term "carboxylated acrylic polymers" is defined to encompass homopolymers, copolymers and terpolymers. If both x =0 and z =0, the polymer of formula (II) is a homopolymer, for example, poly(acrylic acid). If x≠0 and z=0, or x≠0 and z≠0, the polymer of formula (II) is a copolymer, and if x≠0 and z≠0, the polymer of formula (II) is a terpolymer. The carboxylic acrylic polymers represented by formula (II) can be obtained by common synthetic methods known to those having ordinary skill in the art of polymer chemistry, for example, by radical or ionic polymerization or copolymerization of acrylic monomers in bulk, solution, suspension, or emulsion.

The carboxylic acrylic polymers represented by formula (II) can include copolymers with heparin. Such acrylate-heparin copolymers have additional units derived from heparin and can be obtained by copolymerization of acrylic monomers with heparin. The conditions of the process of copolymerization can be determined by those having ordinary skill in the art. Optionally, the carboxylic acrylic polymers represented by formula (II) can be also physically blended with a sulfonated acrylic polymer, for example, with poly(acrylamidomethyl propane sulfonic acid) (AMPS), or with heparin. AMPS has a general formula (III):

(III)

When PArg comes in contact with a carboxylated acrylic polymer of an intermediate polymer layer, the guanidino groups (—NH—C(NH$_2$)=NH) and terminal amino groups of PArg will form ionic association with the carboxyl groups of the acrylic acid component of the carboxylated acrylic polymer. As a result, the intermediate polymer layer will immobilize the PArg molecules, thus retarding the release of PArg.

Typical polymers described by formula (II) can be summarized as shown in Table 1.

As pointed out above, to fabricate the primer layer, the intermediate polymer layers and the topcoat layer, the polymers are dissolved in a solvent or a combination of solvents. Representative examples of some suitable solvents include DMAC, N,N-dimethylformamide(DMF), tethrahydrofurane (THF), cyclohexanone, xylene, toluene, acetone, i-propanol, methyl ethyl ketone, propylene glycol monomethyl ether, methyl butyl ketone, ethyl acetate, n-butyl acetate, and dioxane. Some solvent mixtures can be used as well. Representative examples of the mixtures include:

(1) DMAC and methanol (e.g., 50:50 by mass mixture);
(2) water, i-propanol, and DMAC (e.g., 10:3:87 by mass mixture);
(3) i-propanol and DMAC (e.g., 80:20, 50:50, or 20:80 by mass mixtures);
(4) acetone and cyclohexanone (e.g., 80:20, 50:50, or 20:80 by mass mixtures);
(5) acetone and xylene (e.g., 50:50 by mass mixture); and
(6) acetone, FLUX REMOVER AMS, and xylene (e.g., 10:50:40 by mass mixture).

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of the mixture contains methanol, and trace amounts of nitromethane. Those having ordinary skill in the art will select a solvent or mixture of solvents suitable for a particular polymer being dissolved.

The polycationic peptides can be introduced to form the drug layer alone or blended with other active agent(s). Generally speaking, the active agent can include any substance capable of exerting a therapeutic or prophylactic effect in the practice of the present invention. For example, the active agent could be designed to inhibit the activity of vascular smooth muscle cells. It can be directed at inhibiting abnormal or inappropriate migration and/or proliferation of smooth muscle cells to inhibit restenosis. The drug may include small molecule drugs, peptides, proteins, oligonucleotides, and the like.

Examples of drugs include antiproliferative substances such as actinomycin D, or derivatives and analogs thereof

TABLE 1

Examples of Polyacrylates Described by Formula (II) (X' = H)

| No. | Polyacrylate | Abbreviation | Q | X | Q' | X" | x | y | z |
|---|---|---|---|---|---|---|---|---|---|
| 1 | Poly(n-butyl methacrylate-co-acrylic acid) | P(BMA—AA) | OC$_4$H$_9$ | CH$_3$ | N/A | N/A | 80 | 20 | 0 |
| 2 | Poly(n-butyl methacrylate-co-acrylic acid) | P(BMA—AA) | OC$_4$H$_9$ | CH$_3$ | N/A | N/A | 96.5 | 3.5 | 0 |
| 3 | Poly(n-butyl methacrylate-co-acrylic acid) | P(BMA—AA) | OC$_4$H$_9$ | CH$_3$ | N/A | N/A | 50 | 50 | 0 |
| 4 | Poly(methyl methacrylate-co-acrylic acid-co-n-butyl acrylate) | P(MMA—AA—BA) | OCH$_3$ | CH$_3$ | COOC$_4$H$_9$ | H | 50 | 20 | 30 |
| 5 | Poly(ethyl methacrylate-co-acrylic acid) | P(EMA—AA) | OC$_2$H$_5$ | CH$_3$ | N/A | N/A | 80 | 20 | 0 |
| 6 | Poly(2-ethylhexylacrylate-co-acrylic acid-co-methyl methacrylate) | P(EHA—AA—MMA) | OZ*$^)$ | H | COOCH$_3$ | CH$_3$ | 20 | 20 | 60 |
| 7 | Poly(acrylic acid) | PAA | N/A | N/A | N/A | N/A | 0 | ≧2 | 0 |

*$^)$Z =  —CH$_2$—CH—(CH$_2$)$_3$—CH$_3$ (2-ethylhexyl group, also known as 3-methylheptyl group).
   |
   CH$_2$—CH$_3$ (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. TAXOTERE®, from Aventis S.A., Frankfurt, Germany) methotrexate, azathioprine, vincristine, vinblastine, fluorouracil, doxorubicin hydrochloride (e.g. ADRIAMYCIN® from Pharmacia & Upjohn, Peapack N.J.), and mitomycin (e.g. MUTAMYCIN® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX™ (Biogen, Inc., Cambridge, Mass.). Examples of such cytostatic or antiproliferative agents include angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide-releasing compounds. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of everolimus available from Novartis), 40-O-(3-hydroxy)propyl-rapamycin, 40-O-[2-(2-hydroxy)ethoxy]ethyl-rapamycin, and 40-O-tetrazole-rapamycin.

The coatings and methods of the present invention have been described with reference to a stent, such as a balloon expandable or self-expandable stent. The use of the coating is not limited to stents, however, and the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made: from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Embodiments of the present invention can be further illustrated by the following examples.

DETAILED DESCRIPTION

The outer surface of a bare 13 mm TETRA® stent (available from Guidant Corporation) was thoroughly cleaned by sonication in isopropyl alcohol (applying ultrasound frequency to the stent immersed into the isopropyl alcohol bath) followed by treatment by an argon plasma using techniques and equipment known to those having ordinary skill in the art.

A solution of poly(butyl methacrylate) PBMA in a blend of organic solvents (solution I) was prepared by mixing the following components:

(1) about 5 mass % of PBMA having weight-averaged molecular weight ($M_w$) of about 649,000;

(2) about 35 mass % of toluene;

(3) about 10 mass % of methylethylketone; and (4) the balance, xylene.

A first composition was prepared by mixing the following components:

(a) about 40 mass % of solution I;

(b) about 10 mass % of cyclohexanone;

(c) about 15 mass % of methylethylketone;

(d) about 15 mass % of methylisobutylketone; and (e) the balance, xylene.

Overall, the first composition contained about 2 mass % of PBMA, about 19 mass % of methylethylketone, about 15 mass % of methylisobutylketone, about 14 mass % of toluene, about 10 mass % of cyclohexanone, and the balance, xylene.

The first composition was applied onto the surface of the stent by spraying and dried to form a primer layer. A spray coater was used, having a 0.014 fan nozzle maintained at about 60° C. with a feed pressure of about 0.2 atm (about 3 psi) and an atomization pressure of about 1.3 atm (about 20 psi). The primer was baked at about 140° C. for about 2 hours, yielding a dry primer layer. The total amount of solids of the primer layer was about 40 μg. "Solids" means the amount of the dry residue deposited on the stent after all volatile organic compounds (e.g., the solvent) have been removed.

A second composition was prepared by mixing the following components:

(a) about 1.9 mass % of R7 acetate;

(b) about 1.0 mass % of DMSO;

(c) about 1.5 mass % of DMAC;

(d) about 0.6 mass % of dimethylethanolamine (DMEA);

(e) about 38 mass % of distilled sterile water; and (f) the balance, methanol.

The second composition was applied onto the dried primer layer to form a first drug layer, using the same spraying technique and equipment as those used for applying the primer layer, followed by drying. The total amount of solids of the first drug layer was about 30 µg.

A solution of P(BMA-AA) copolymer in a blend of organic solvents (solution II) was prepared, by mixing the following components:
(1) about 4 mass % of P(BMA-AA) copolymer containing about 80 molar % units derived from butyl methacrylate and about 20 molar % units derived from acrylic acid, the P(BMA-AA) copolymer having $M_w$ of about 340,000;
(2) about 38 mass % of toluene;
(3) about 10 mass % of methylisobutylketone;
(4) about 10 mass % of cyclohexanone; and
(5) the balance, xylene.

A third composition was prepared by mixing the following components:
(a) about 50 mass % of solution II;
(b) about 10 mass % of cyclohexanone;
(c) about 5 mass % of toluene;
(d) about 29 mass % of methylisobutylketone; and
(e) the balance, xylene.

Overall, the third composition contained about 2 mass % of P(BMA-AA) polymer, about 34 mass % of methylisobutylketone, about 24 mass % of toluene, about 15 mass % of cyclohexanone, and the balance, xylene.

The third composition was applied onto the dried first drug layer to form a first intermediate layer. The same spraying technique and equipment as those used for applying the primer layer and the first drug layer were used, followed by drying, e.g., by baking as described above. The total amount of solids of the first intermediate layer was about 40 µg.

A fourth composition was prepared by mixing the following components:
(a) about 1.9 mass % of R7 acetate;
(b) about 1.0 mass % of DMSO;
(c) about 1.5 mass % of DMAC;
(d) about 0.6 mass % of DMEA;
(e) about 38 mass % of distilled sterile water; and
(f) the balance, methanol.

The fourth composition was applied onto the dried first intermediate layer to form a second drug layer, using the same spraying technique and equipment as those used for applying the first drug layer, followed by drying. The total amount of solids of the second drug layer was about 30 µg.

A fifth composition identical to the third composition described above and containing the same grade of the P(BMA-AA) copolymer was applied onto the dried second drug layer to form a second intermediate layer. The same spraying technique and equipment as those used for applying the first intermediate layer were used, followed by drying (e.g., baking) as described above. The total amount of solids of the second intermediate layer was about 40 µg.

A sixth composition identical to the fourth composition was prepared and applied onto the second intermediate layer to form a third drug layer. The third drug layer was dried as described above and a seventh composition identical to the third and the fifth compositions described above, containing the same grade of the P(BMA-AA) copolymer was applied onto the dried third drug layer to form a third intermediate layer.

An eighth composition was prepared by mixing the following components:
(a) about 40 mass % of the PBMA solution (solution I described above);
(b) about 10 mass % of cyclohexanone;
(c) about 15 mass % of methylethylketone;
(d) about 15 mass % of methylisobutylketone; and
(e) the balance, xylene.

Overall, the sixth composition contained about 2 mass % of PBMA, about 19 mass % of methylethylketone, about 15 mass % of methylisobutylketone, about 14 mass % of toluene, about 10 mass % of cyclohexanone, and the balance, xylene.

The sixth composition was applied onto the dried third intermediate layer to form a topcoat layer. The same spraying technique and equipment as those used for applying the primer layer were used, followed by drying, e.g., by baking as described above. The total amount of solids of the topcoat layer was about 200 µg.

EXAMPLE 2

Figure 2:
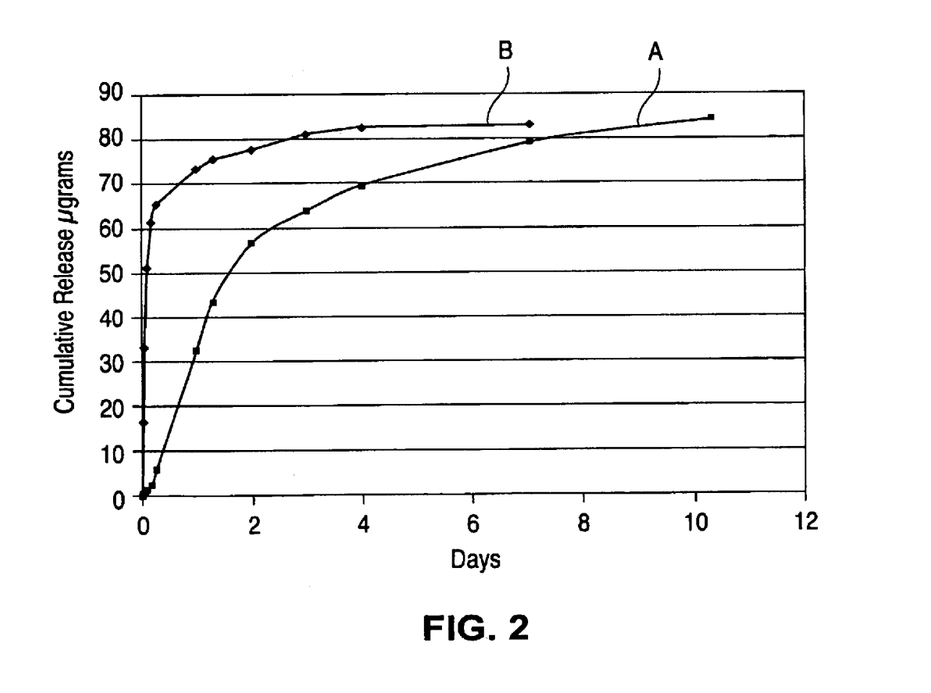
FIG. 2 is a chart showing a profile of release of a drug from a stent coating fabricated according to an embodiment of the present invention.

Stents coated as described above were tested for cumulative amount of the drug released. The stents were immersed in a phosphate buffered saline solution having 1 mass % of sodium dodecyl sulfate. A sample of the solution was taken every 24 hours and analyzed chromatographically (by HPLC) for the amount of R7 released. As seen from the release profile shown by FIG. 2, the rate of release from the sandwich coating (curve A) was substantially slower than for a control coating (curve B), particularly within the initial period of exposure of the stent to the buffer solution. The control coating comprised a EVAL matrix incorporating R7, where the amount of R7 was about 25 mass % of the dry matrix.

EXAMPLE 3

The stent was coated with a primer layer and a first drug layer as described in Example 1. A solution of P(BMA-AA) copolymer in a blend of organic solvents (solution III) was prepared, by mixing the following components:
(1) about 5 mass % of P(BMA-AA) copolymer containing about 96.5 molar % units derived from butyl methacrylate and about 3.5 molar % units derived from acrylic acid, the P(BMA-AA) polymer having M, of about 340,000; and
(2) the balance, DMAC.

A first composition was prepared by mixing the following components:
(a) about 40 mass % of the P(BMA-AA) polymer solution (solution III described above);
(b) about 25 mass % of methylethylketone;
(c) about 25 mass % of methylisobutylketone; and
(d) the balance, xylene.

Overall, the first composition contained about 2 mass % of P(BMA-AA) polymer, about 38 mass % of DMAC, about 25 mass % of methylisobutylketone, about 25 mass % of methylethylketone, and the balance, xylene.

The first composition was applied onto the dried first drug layer to form a first intermediate layer. The total amount of solids of the first intermediate layer was about 40 µg. The second drug layer was then formed on the first intermediate layer as described in Example 1.

The process of forming the first drug layer and the first intermediate layer was repeated twice to form the second drug layer, the second intermediate layer, the third drug layer, and the third intermediate layer.

The topcoat layer was then formed on the third intermediate layer as described in Example 1.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a coating for an implantable medical device, comprising:
   (a) depositing a layer including a polycationic peptide on the device; and
   (b) depositing a layer including a carboxylated acrylic polymer over the layer including the polycationic peptide.

2. The method of claim 1, additionally including depositing a primer layer on the surface of the device and beneath the layer including the polycationic peptide.

3. The method of claim 1, additionally including depositing a layer including the carboxylated acrylic polymer beneath the layer including the polycationic peptide.

4. The method of claim 1, additionally including depositing a topcoat layer over the layer including the carboxylated acrylic polymer.

5. The method of claim 4, wherein the topcoat layer is fabricated of a polymer selected from a group consisting of poly(ethylene-co-vinyl alcohol), polyacrylates, and blends thereof.

6. The method of claim 1, wherein the implantable medical device is a stent.

7. The method of claim 1, wherein the polycationic peptide includes poly(L-arginine), poly(D-arginine), poly(D,L-arginine), poly(L-lysine), poly(D-lysine), poly(δ-guanidino-α-aminobutyric acid), or a mixture of poly(L-arginine) and poly(D-arginine).

8. The method of claim 1, wherein the carboxylated acrylic polymer has a formula wherein each X, X', and X" is independently, a hydrogen atom or an alkyl group; Q is an alkoxy group or 2-amino-2-methyl propane sulfonyl group; Q' is an unsubstituted or substituted phenyl group or a carboxy group; each R and R' is independently a $C_1$ to $C_{12}$ straight chained or branched aliphatic radical; and x, y, and z are integers, where y≠0.

9. The method of claim 1, wherein the carboxylated acrylic polymer includes units derived from heparin.

10. The method of claim 1, additionally including blending the carboxylated acrylic polymer with a compound selected from a group consisting of a sulfonated acrylic polymer, heparin, and mixtures thereof, prior to depositing the layer including the carboxylated acrylic polymer.

11. The method of claim 10, wherein the sulfonated acrylic polymer is poly(acrylamidomethyl propane sulfonic acid).

12. A coating for an implantable medical device, comprising a region including a carboxylated acrylic polymer disposed over a region including a polycationic peptide.

13. The coating of claim 12, wherein the implantable medical device is a stent.

14. The coating of claim 12, wherein the carboxylated acrylic polymer has a formula wherein each X, X', and X" is independently a hydrogen atom or an alkyl group; Q is an alkoxy group or 2-amino-2-methyl propane sulfonyl group; Q' is an unsubstituted or substituted phenyl group or a carboxy group; each R and R' is independently a $C_1$ to $C_{12}$ straight chained or branched aliphatic radical; and x, y, and z are integers, where y≠0.

15. The coating of claim 12, wherein the carboxylated acrylic polymer includes units derived from heparin.

16. The coating of claim 12, additionally including a compound selected from a group consisting of a sulfonated acrylic polymer, heparin, and mixtures thereof, blended with the carboxylated acrylic polymer.

17. The coating of claim 16, wherein the sulfonated acrylic polymer is poly(acrylamidomethyl propane sulfonic acid).

18. The coating of claim 12, wherein the polycationic peptide includes poly(L-arginine), poly(D-arginine), poly(D,L-arginine), poly(L-lysine), poly(D-lysine), poly(δ-guanidino-α-aminobutyric acid), or a mixture of poly(L-arginine) and poly(D-arginine).

19. The coating of claim 12, additionally including a polymeric region free from any polycationic peptides disposed beneath the region including the polycationic peptide.

20. The coating of claim 19, wherein the polymeric region includes a carboxylated acrylic polymer.

21. The coating of claim 20, wherein the carboxylated acrylic polymer has a formula wherein each X, X', and X" is independently, a hydrogen atom or an alkyl group; Q is an alkoxy group or 2-amino-2-methyl propane sulfonyl group; Q' is an unsubstituted or substituted phenyl group or a carboxy group; each R and R' is independently a $C_1$ to $C_{12}$ straight chained or branched aliphatic radical; and x, y, and z are integers, where y≠0.

22. The coating of claim 19, wherein the polymeric region is disposed on a surface of the implantable medical device.

* * * * *